(12) United States Patent
Huffenus et al.

(10) Patent No.: US 10,123,815 B2
(45) Date of Patent: Nov. 13, 2018

(54) SURGICAL KNIFE

(71) Applicant: PRECISION ENGINEERED PRODUCTS, LLC, Attleboro, MA (US)

(72) Inventors: Alan Michael Huffenus, South Easton, MA (US); Gregory Bernard Blumenthal, North Providence, RI (US)

(73) Assignee: Precision Engineered Products, LLC, Attleboro, MA (US)

( * ) Notice: Subject to any disclaimer, the term of this patent is extended or adjusted under 35 U.S.C. 154(b) by 209 days.

(21) Appl. No.: 14/622,171

(22) Filed: Feb. 13, 2015

(65) Prior Publication Data
US 2016/0235430 A1    Aug. 18, 2016

(51) Int. Cl.
*A61B 17/32*   (2006.01)
*A61B 17/3211*   (2006.01)

(52) U.S. Cl.
CPC .. *A61B 17/320016* (2013.01); *A61B 17/3211* (2013.01); *A61B 2017/32113* (2013.01)

(58) Field of Classification Search
CPC ........ A61B 17/320016; A61B 17/3211; A61B 2017/32113
See application file for complete search history.

(56) References Cited

U.S. PATENT DOCUMENTS

| | | |
|---|---|---|
| 3,905,101 A | 9/1975 | Shepherd |
| 3,945,117 A | 3/1976 | Beaver |
| 4,414,974 A | 11/1983 | Dotson et al. |
| 4,491,132 A | 1/1985 | Aikins |
| 4,523,379 A | 6/1985 | Osterhout et al. |
| 4,735,202 A | 4/1988 | Williams |
| 4,759,363 A | 7/1988 | Jensen |
| 5,071,426 A | 12/1991 | Dolgin et al. |
| 5,139,507 A | 8/1992 | Dolgin et al. |
| 5,250,063 A | 10/1993 | Abidin et al. |
| 5,250,064 A | 10/1993 | Schneider |
| 5,254,128 A | 10/1993 | Mesa |
| 5,275,606 A | 1/1994 | Abidin et al. |
| 5,299,357 A | 4/1994 | Wonderley et al. |
| 5,309,641 A | 5/1994 | Wonderley et al. |
| 5,330,492 A | 7/1994 | Haugen |
| 5,330,494 A | 7/1994 | van der Westhuizen et al. |
| 5,411,512 A | 5/1995 | Abidin et al. |
| 5,417,704 A | 5/1995 | Wonderley |
| 5,423,843 A * | 6/1995 | Werner ............. A61B 17/3211 30/162 |
| 5,496,340 A | 3/1996 | Abidin et al. |
| 5,527,329 A | 6/1996 | Gharibian |
| 5,569,281 A | 10/1996 | Abidin et al. |
| 5,620,454 A | 4/1997 | Pierce et al. |
| 5,662,669 A | 9/1997 | Abidin et al. |
| 5,676,677 A | 10/1997 | Landis et al. |
| 5,683,407 A | 11/1997 | Jolly et al. |

(Continued)

*Primary Examiner* — Julie A Szpira
(74) *Attorney, Agent, or Firm* — Ohlandt, Greeley, Ruggiero & Perle, L.L.P.

(57) ABSTRACT

A surgical knife is provided. The knife has a blade, a handle, an elongated tube connected to the blade and the handle, and a sheath slidable over the tube and blade. The sheath is moveable from a first position that exposes the blade to and second position that conceals the blade. The blade, handle, and tube are in a fixed rigid relationship with each other while the sheath is movable.

27 Claims, 15 Drawing Sheets

(56) References Cited

U.S. PATENT DOCUMENTS

| | | |
|---|---|---|
| 5,752,968 A | 5/1998 | Jolly et al. |
| 5,827,309 A | 10/1998 | Jolly et al. |
| 5,868,771 A | 2/1999 | Herbert et al. |
| 5,919,201 A | 7/1999 | Carter et al. |
| 5,938,675 A | 8/1999 | Gharibian |
| 5,938,676 A | 8/1999 | Cohn et al. |
| 6,053,929 A | 4/2000 | Cohn et al. |
| 6,500,187 B1 * | 12/2002 | Petersen ............ A61B 17/3213 30/329 |
| 6,569,175 B1 | 5/2003 | Robinson |
| 6,626,925 B2 | 9/2003 | Newman et al. |
| 6,629,985 B1 | 10/2003 | Kiehne |
| 6,884,240 B1 | 4/2005 | Dykes |
| 7,022,128 B2 | 4/2006 | Morawski et al. |
| 7,087,067 B2 | 8/2006 | Kehr et al. |
| 7,153,317 B2 | 12/2006 | Kanodia et al. |
| 7,172,611 B2 | 2/2007 | Harding et al. |
| 7,346,989 B2 | 3/2008 | Shi |
| 7,387,637 B2 | 6/2008 | Morawski et al. |
| 7,810,241 B2 | 10/2010 | Pooler |
| 7,857,824 B2 | 12/2010 | Kiehne |
| 7,901,422 B2 | 3/2011 | Morawski et al. |
| 7,905,894 B2 | 3/2011 | Morawski et al. |
| 7,909,840 B2 | 3/2011 | Cote et al. |
| RE42,507 E | 6/2011 | Wilkinson et al. |
| 8,025,692 B2 * | 9/2011 | Feeser .................... A61F 2/966 604/264 |
| 8,114,103 B2 | 2/2012 | Rasco |
| 8,167,897 B2 | 5/2012 | Muto et al. |
| 8,256,331 B2 | 9/2012 | Auchter et al. |
| 8,282,662 B2 | 10/2012 | Reaux |
| 8,409,232 B2 | 4/2013 | Muto et al. |
| 8,465,512 B2 | 6/2013 | Rosenhan |
| 8,567,072 B2 | 10/2013 | Yi et al. |
| 2004/0186496 A1 | 9/2004 | Sandel et al. |
| 2005/0119680 A1 | 6/2005 | Dykes |
| 2006/0212058 A1 | 9/2006 | Djordjevic et al. |
| 2007/0255298 A1 | 11/2007 | Djordjevic et al. |
| 2009/0131963 A1 | 5/2009 | Rasco |
| 2009/0192538 A1 | 7/2009 | Sandel et al. |
| 2010/0146799 A1 | 6/2010 | Hoffman et al. |
| 2011/0092995 A1 | 4/2011 | Cote et al. |
| 2011/0092996 A1 | 4/2011 | Morawski et al. |
| 2011/0270291 A1 | 11/2011 | Nakamura |
| 2012/0083816 A1 | 4/2012 | Hajgato et al. |
| 2013/0079804 A1 | 3/2013 | Milton et al. |
| 2013/0204284 A1 | 8/2013 | Morawski et al. |
| 2013/0331871 A1 | 12/2013 | Milton et al. |

* cited by examiner

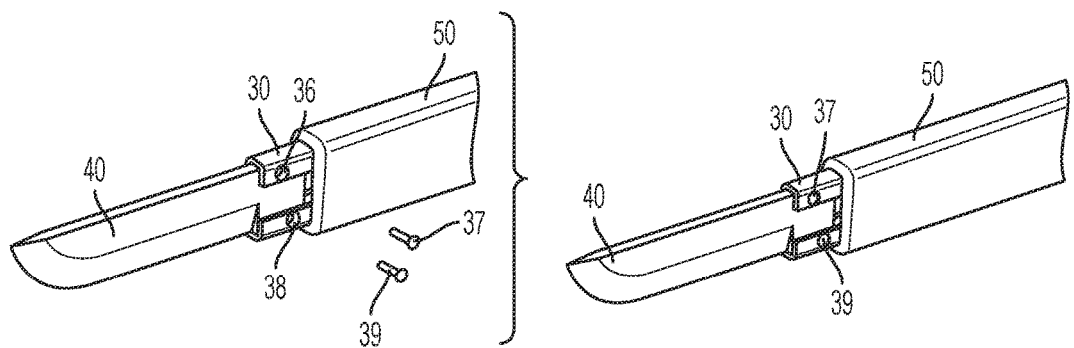
FIG. 17
FIG. 18
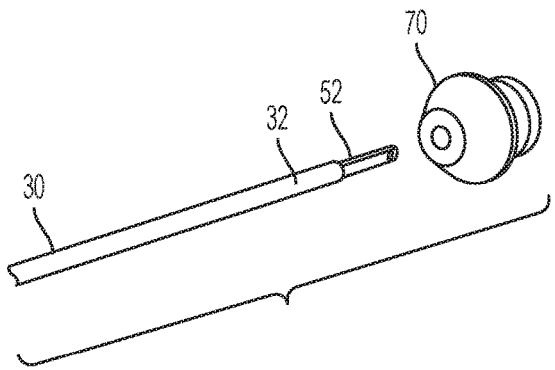
FIG. 19
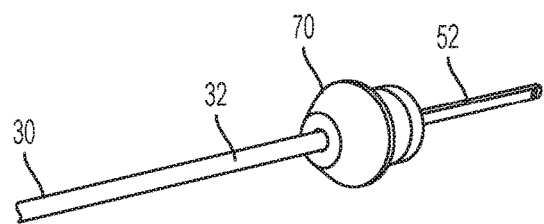
FIG. 20

SURGICAL KNIFE

BACKGROUND OF THE DISCLOSURE

1. Field of the Disclosure

The present disclosure relates to a surgical instrument. More particularly, the present disclosure relates a surgical instrument that is a knife with a blade that avoids movement once positioned. Such a knife can be used during, for example, laparoscopic surgery.

2. Description of Related Art

Surgical knives are sometimes equipped with a sheath that has a blade extendable beyond the coverage of a protected sheath. In use, a surgeon will actuate a mechanism that causes a knife blade to project out from or back into a protective sheath. Thus, a surgeon will position the knife in the vicinity of a site where a cut is to be made prior to the incision or cut. Then, the surgeon will actuate the knife, urging the knife blade toward the site.

As well known in the art, surgical procedures require use of surgical instruments including surgical knives in a precise manner. The aforementioned sheathed knives have an inherent imprecision. More specifically, since the knife blade is movable, a surgeon cannot use the handle to precisely locate the blade at a desired surgical point of incision, but instead can only position the sheath near the desired surgical incision point. Further, such a knife also has an inherent spring back movement. This movement hampers precision alignment.

Presently, surgeons deal with the aforementioned shortcomings in at least two ways. The first way involves the surgeon positioning the knife close to a desired incision or cut location. The surgeon will estimate the distance the knife blade will protrude from the protective sheath. The surgeon will then move the sheath to approximately this distance. Next, the surgeon will slowly extend the blade from the sheath toward the cut location, visually monitoring and physically compensating for any imprecision in the estimated distance. The second way that surgeons deal with the aforementioned shortcomings of surgical knives involves the surgeon positioning the sheath tip at the location of the desired incision. Then, the surgeon will simultaneously urge the knife blade towards the surgical site and move the handle of the knife away from the surgical site, again visually monitoring and physically compensating for any imprecisions in movement.

Accordingly, there is a need for a surgical knife that prevents movement and forces on the knife blade and that allows a surgeon to position the knife with better precision than heretofore.

BRIEF SUMMARY OF THE DISCLOSURE

The present disclosure provides a surgical knife that has a blade that provides for more precise alignment with the incision site.

The present disclosure further provides such a surgical knife that avoids unwanted movement of the blade once positioned at the incision site.

The present disclosure also provides such a surgical knife having a sheath that is retractable from a first position to uncover the blade of the surgical knife and extendable to a second position to cover the blade.

The present disclosure further provides such a surgical knife having the blade, the sheath, a handle, and a slide in the handle. In a preferred embodiment, the slide is attached to a flexible wire that travels in a tube that has the sheath at the working end thereof.

The present disclosure yet further provides such a surgical knife that when a surgeon actuates the slide for use, the sheath moves back to expose the blade of the surgical knife.

Accordingly, the present disclosure provides a surgical knife in which the blade is always in a rigid fixed position with respect to the handle of the surgical knife even during use of the surgical knife by the surgeon. Thus, any blade replicates the exact movement of the surgeon's hand.

The present disclosure still further provides such a surgical knife in which the blade itself is placed in the exact incision position by the surgeon prior to incision.

The present disclosure additionally provides a surgical knife having a blade mechanically connected to a fixed tube, which connection eliminates potential debris or loose material in the instrument that importantly minimizes the risk that such unwanted debris or materials could be left in the body during surgery.

In an exemplary embodiment, the surgical knife has a handle, a blade, an elongated tube with a distal end and a proximal end, with the distal end connected to the blade and the proximal end connected to the handle, and a sheath that is slidable over the tube and blade. The sheath is at least as long as the blade, and is movable linearly from a first or retracted position in which the blade is exposed to a second or extendable position in which the blade is concealed. The blade, handle, and tube are always in a fixed, rigid relationship with each other even during movement of the sheath.

The above-described and other features and advantages of the present disclosure will be appreciated and understood by those skilled in the art from the following detailed description, drawings, and appended claims.

BRIEF DESCRIPTION OF THE SEVERAL VIEWS OF THE DRAWINGS

FIG. 17 is a perspective view of an assembly of the blade mount.

FIG. 18 is a second perspective view of an assembly of the blade mount.

FIG. 19 is an exploded assembly view of the front cap.

FIG. 20 is an assembled view of the assembly of the front cap of FIG. 19.

A component or feature that is common to more than one drawing is indicated with the same reference number in each drawing.

DETAILED DESCRIPTION OF THE DISCLOSURE

Figure 1:
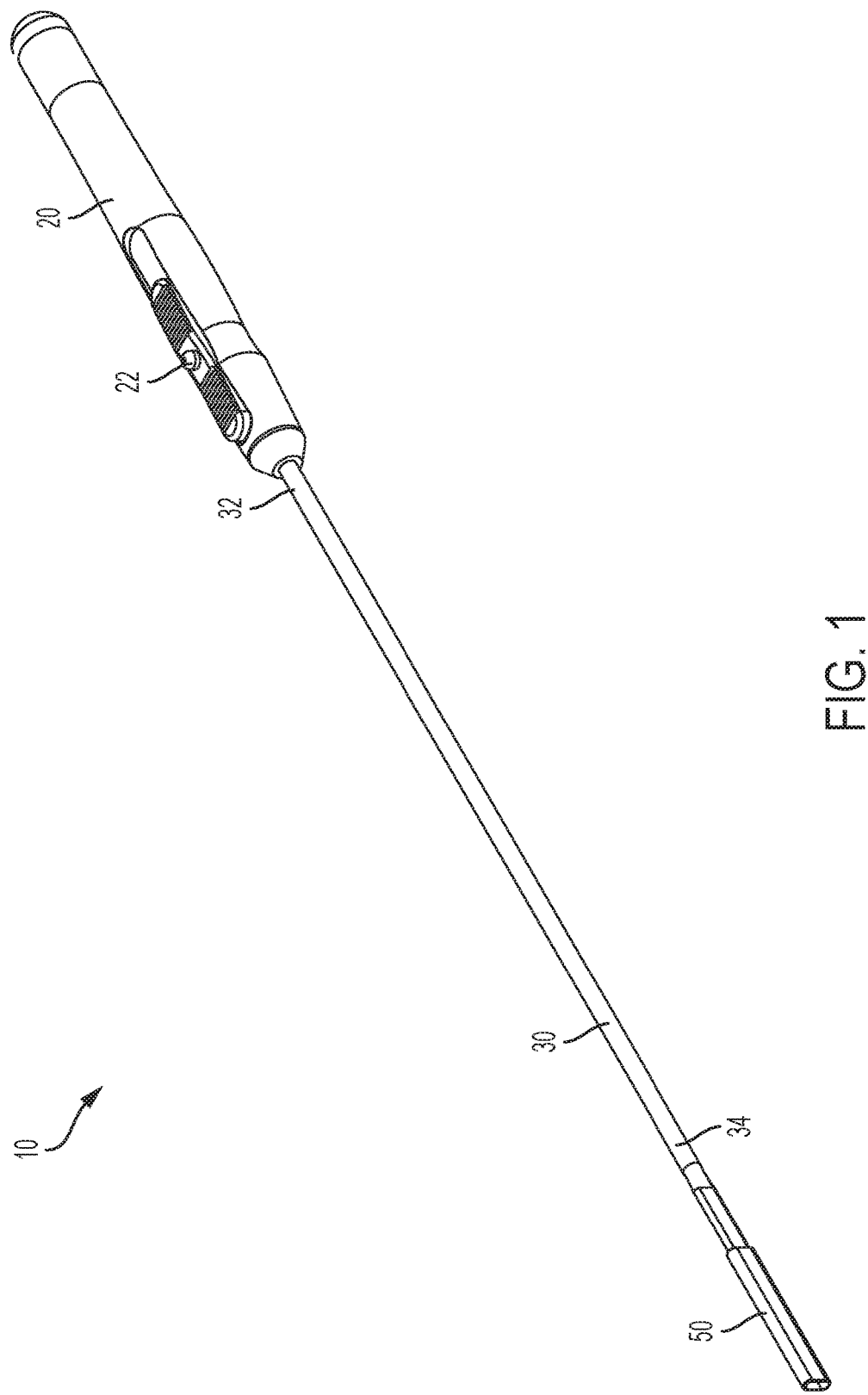
FIG. 1 is a perspective view of the surgical knife of the present disclosure.
Figure 2:
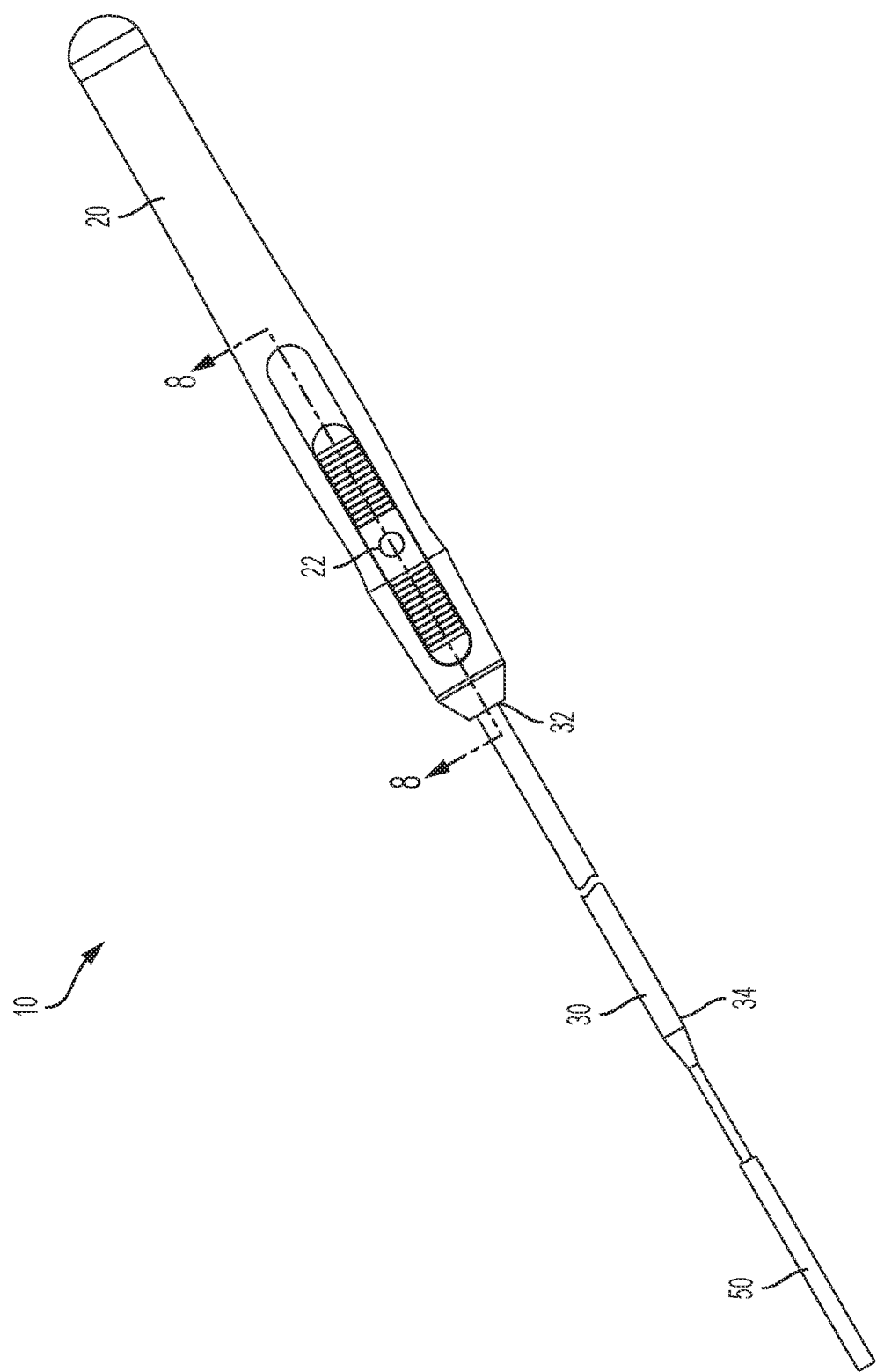
FIG. 2 is a top view of the surgical knife of FIG. 1.
Figure 3:
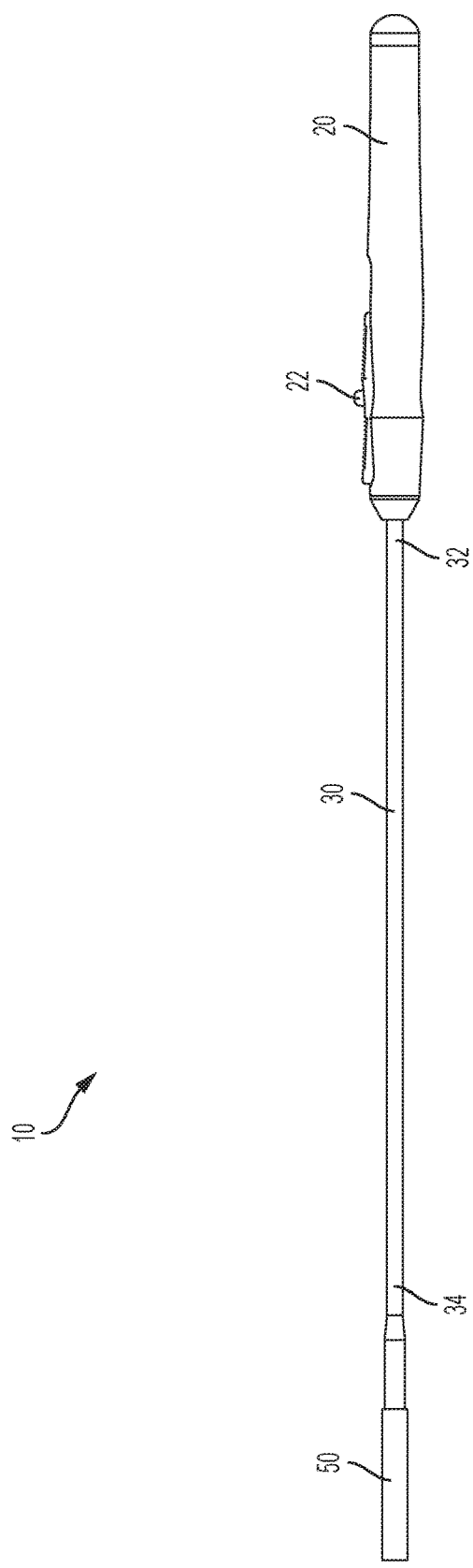
FIG. 3 is a side view of the surgical knife of FIG. 1.
Figure 4:
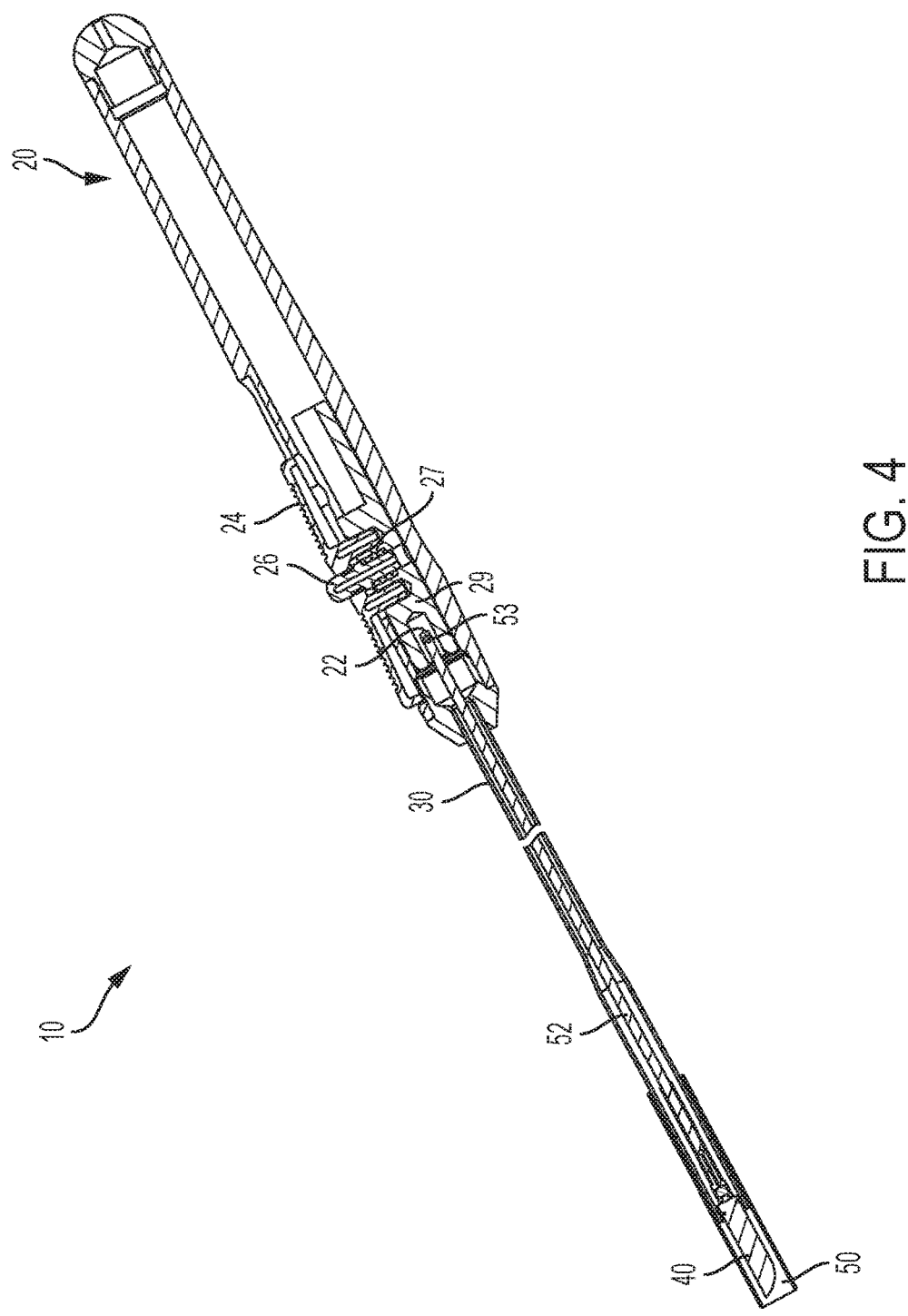
FIG. 4 is a cross section view of the surgical knife of FIG. 2 taken at A-A.
Figure 5:
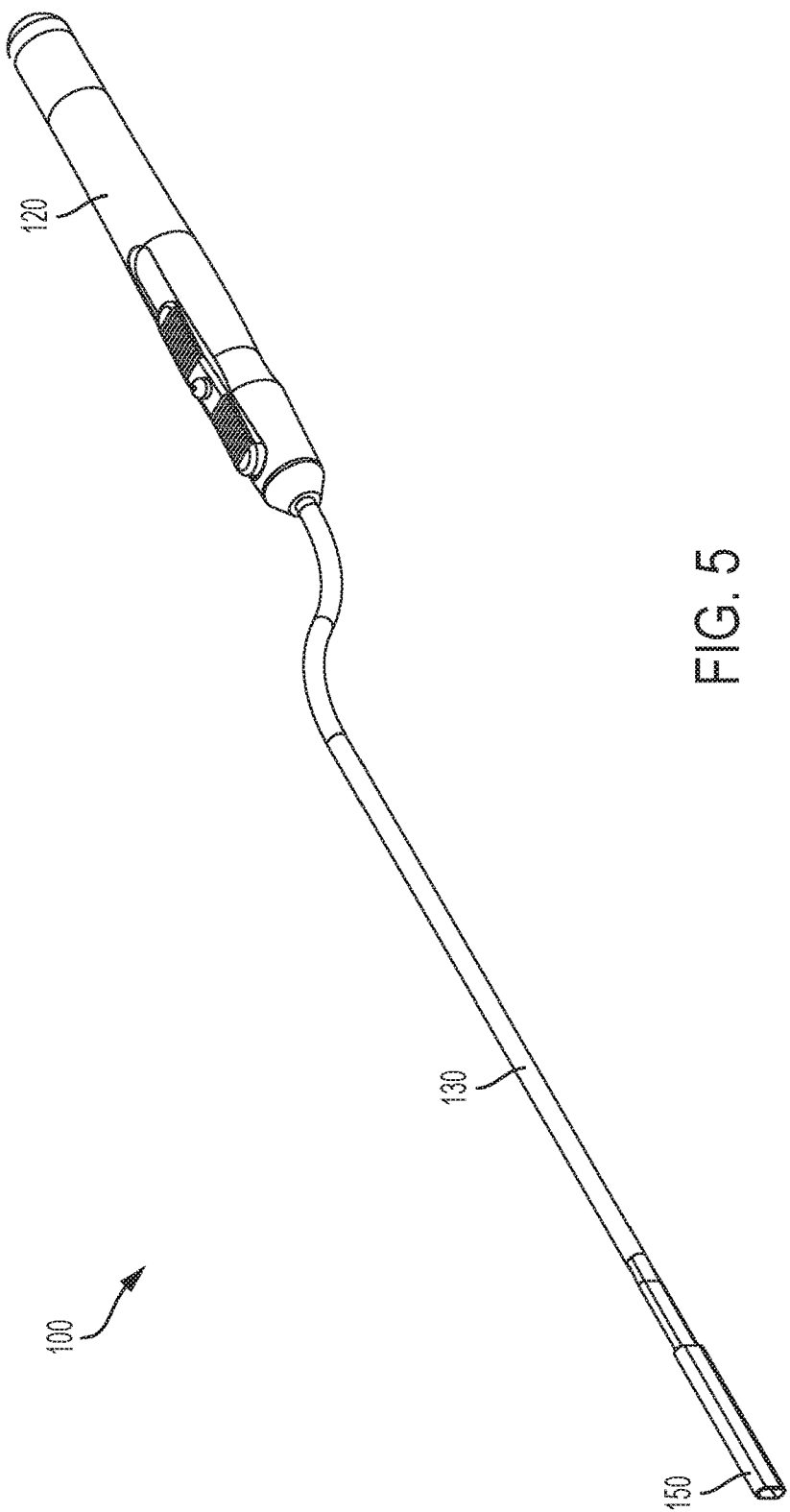
FIG. 5 is a perspective view of an alternative embodiment of the surgical knife of the present disclosure.
Figure 6:
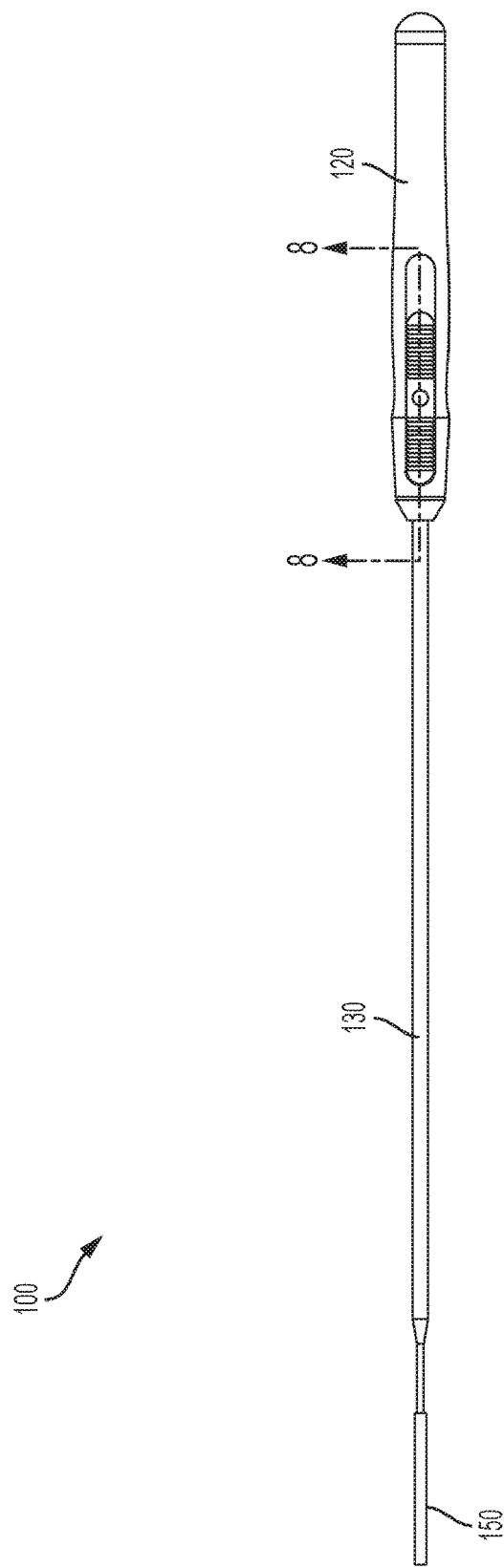
FIG. 6 is a top view of the surgical knife of FIG. 5.
Figure 7:
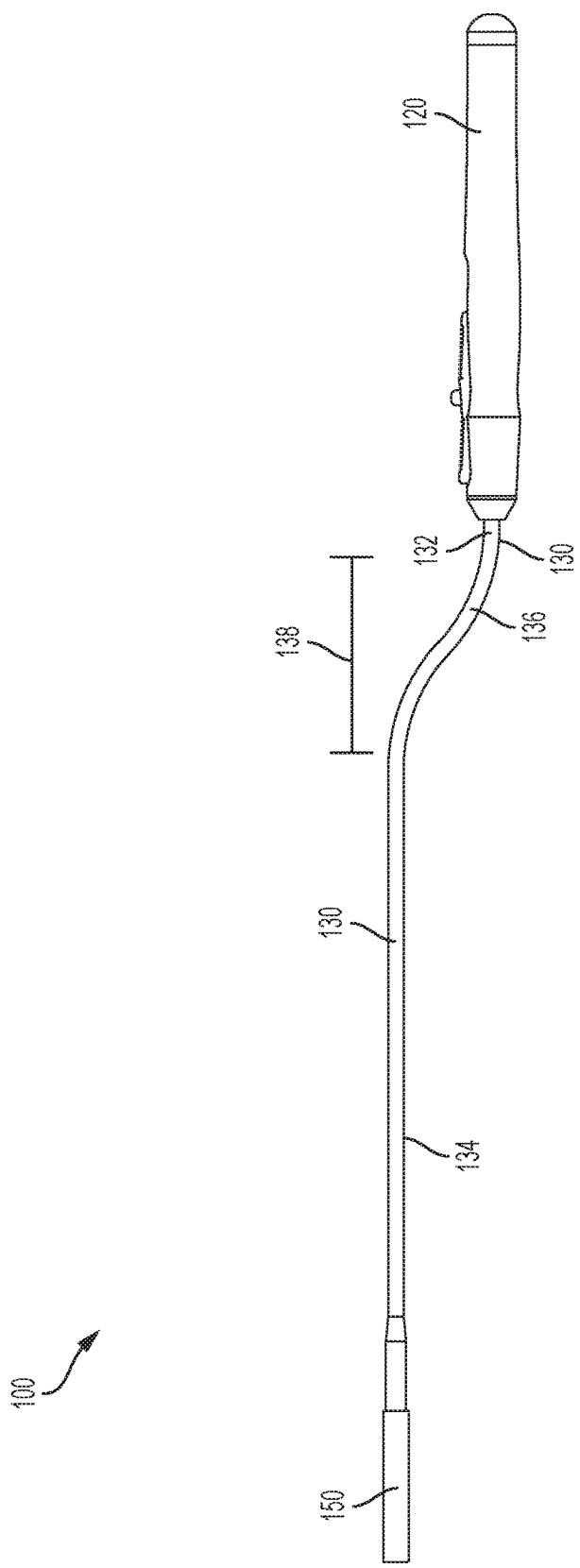
FIG. 7 is a side view of the surgical knife of FIG. 5.
Figure 8:
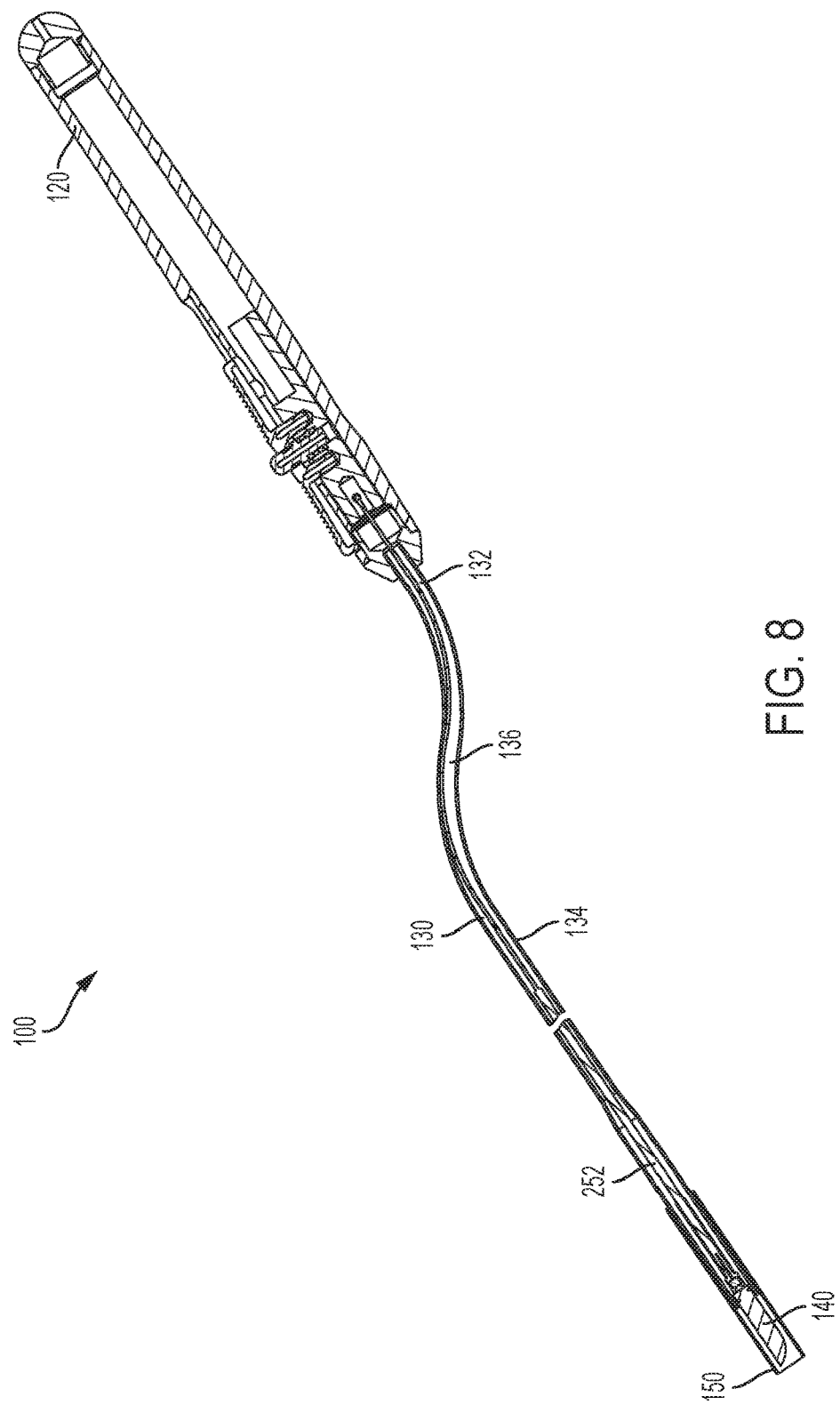
FIG. 8 is a cross section view of the surgical knife of FIG. 6 taken at B-B.

Referring to the drawings and in particular to FIGS. 1-4, there is shown a surgical knife according to the present disclosure generally represented by reference numeral 10. Knife 10 has a handle 20, a tube 30, a blade 40, and a sheath 50. Tube 30 has a proximal end 32 and a distal end 34. Tube 30 connects to handle 20 at proximal end 32, and connects to blade 40 at distal end 34. Sheath 50 surrounds both tube 30 and blade 40. As shown clearly in FIG. 4, sheath 50 is operatively connected by a wire 52 to an actuator 22 on or in handle 20, such that when actuated, sheath 50 retracts to expose blade 40, or sheath 50 extends to conceal blade 40. Advantageously, blade 40 is held in rigid relationship to handle 20. Significantly, there is no movement of blade 40 relative to handle 20. Thus, movement of the handle 20 by the surgeon results in direct movement of blade 40 at the surgical or incision site.

Tube 30 is a linear conduit through which wire 52 travels, thereby controlling the movement of sheath 50. Tube 30 has a length of about 6 inches to about 20 inches. In a preferred embodiment, tube 30 has a length of about 7 inches to about 16 inches, and, in a most preferred embodiment, a length of about 9 inches to about 12 inches. Tube 30 has a diameter from about 0.05 inches to about 0.5 inches. In a preferred embodiment, the diameter is about 0.06 inches to about 0.4 inches, and, in a most preferred embodiment, the diameter is about 0.07 inches to about 0.3 inches.

As used herein, a wire is a flexible cylindrical or rectangular strand or rod made of metal or plastic. Wire 52 has a smaller outer diameter than the inner diameter of tube 30 to allow smooth unimpeded movement therethrough. Wire 52 can be rectangular or flat, as shown, or round, not shown.

When wire 52 is flat, in a preferred embodiment, the wire has a depth of about 0.016 inches to about 0.032 inches and width of about 0.040 inches to about 0.095 inches. In a more preferred embodiment, wire 52 has a depth of about 0.018 inches to about 0.030 inches and width of about 0.047 inches to about 0.087 inches. In a most preferred embodiment, wire 52 has a depth of about 0.020 inches to about 0.028 inches and width of about 0.055 inches to about 0.80 inches. When wire 52 is round, in a preferred embodiment, the diameter is about 0.020 inches to about 0.110 inches, in a more preferred embodiment, the diameter is about 0.040 inches to about 0.090 inches, and in a most preferred embodiment, the diameter is about 0.050 inches to about 0.080 inches. In this context, i.e., wire 52, the term about means plus or minus 20%, preferably plus or minus 15%, and most preferably, plus or minus 10%.

As discussed above, since blade 40 is held in rigid relationship to handle 20, there is no movement of blade 40 relative to handle 20. Sheath 50 retracts to allow the surgeon to operate knife 10 with a higher degree of precision compared to conventional surgical knives since movement of the sheath does not result in movement of blade 40 at the surgical or incision site.

Referring to FIGS. 5-8, there is shown an alternative embodiment of knife 10, generally represented by reference numeral 100. Knife 100 is similar to knife 10, except knife 100 has a tube 130 instead of tube 30. Tube 130 is curved while tube 30 is straight. More particularly, tube 130 is shaped like a bayonet or s-curved having two straight parallel portions 132 and 134. Portion 132 and 134 are spaced apart by a distance 138. Distance 138 can be from about 0.05 inches to about 1.5 inches, preferably from about 0.8 inches to about 1.25 inches, and most preferably from about 0.9 inches to about 1.1 inches. Portion 132 and 134 are preferably in offset parallel planes. A bend 136 joins portion 132 and 134 to form tube 130. Bend 136 should have a radius that is large enough and sufficient to allow smooth movement of wire 252 therethrough without impeding movement.

Analogous to knife 10, knife 100 has a blade 140. Blade 140, like blade 40, can be made from hardened steel, tempered steel, stainless steel, high carbon steel, ceramic, titanium, and analogous materials. For applications where metal cannot be used, such as when used in conjunction with Magnetic Resonance Imaging, blades 40 and 140 can be coated with titanium carbide, zirconium nitride, titanium nitride, boron carbide, silicon based coatings, parylene, polymer based coatings, and the like. Depending on the particular application, blade 140 can take various shapes and forms. For example, blade 140 can have a curved cutting edge, a triangular cutting edge, a flat cutting edge, a crescent shaped cutting edge, a chisel shaped edge, and the like.

Sheaths 50 and 150 can be plastic or metal. For certain applications, a soft sheath will be preferred by the surgeon. Plastic is softer than metal and thus presents less risk to collateral soft tissue. Metal is more durable and thus can be more desirable for long repetitive procedures. Cost and application considerations can also be taken into account.

Handles 20 and 120 can also be metal or plastic. For certain applications, a plastic handle will be preferred by the surgeon. Additionally, the difference in materials can yield various price points.

Figure 9:
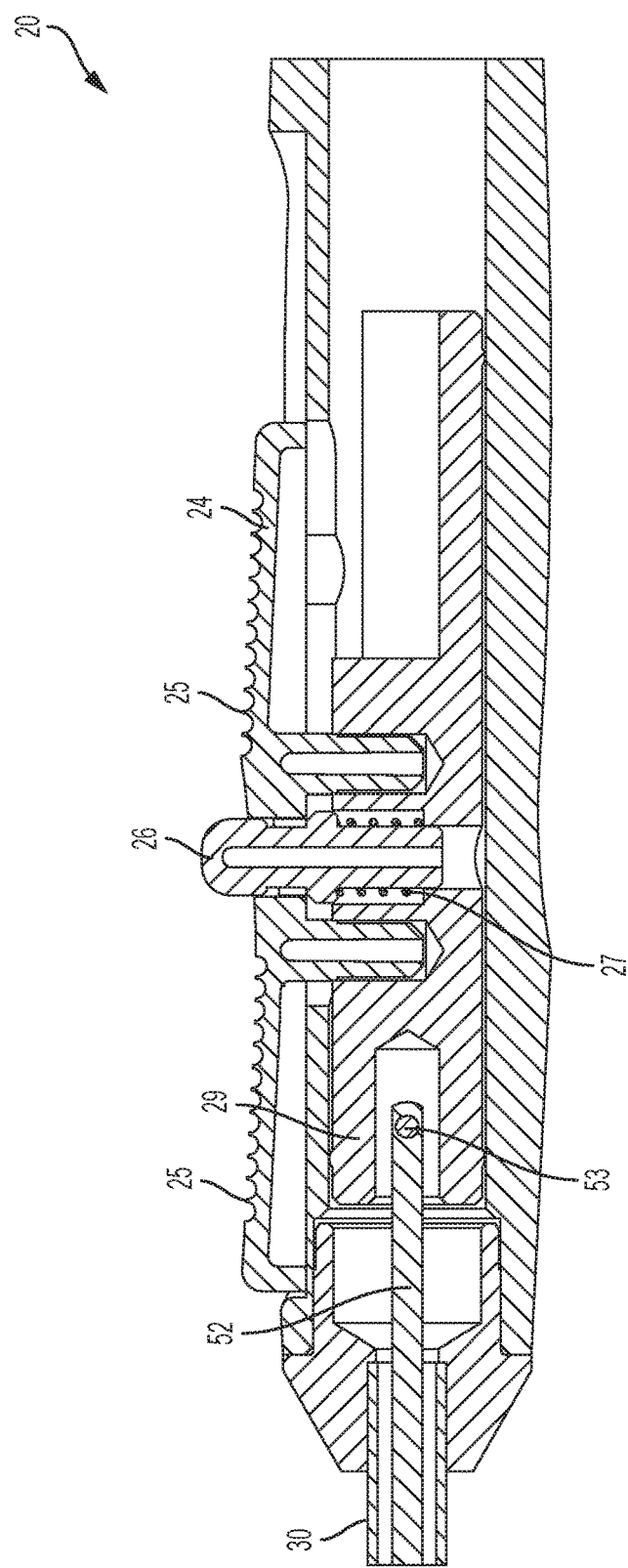
FIG. 9 is a cross section view of the surgical knife of FIG. 2 taken at A-A with the sheath extended.

Referring back to FIG. 4, there is shown a cross section A-A of knife 10, and in FIG. 9, the same cross section of handle 20. Actuator 22 comprises a ribbed slide 24, a button 26, a spring 27, and an inner slide 29. Inner slide 29 is connected to a proximal end of wire 52 by a pin through a hole 53 in wire 52 or a tab portion connected thereto. Thus, as inner slide 29 moves, wire 52 moves identically causing sheath 50 to move the same.

Advantageously, ribbed slide 24 has one or more ridges, notches, ribs, or some pattern 25 that provides a tactile feel and grip to a surgeon operating with knife 10.

The following illustrates an exemplary embodiment of knife 10 and knife 100 of the present disclosure. This discussion will refer to knife 10, although it is equally applicable to knife 100 unless noted to the contrary. Sheath 50 has three different positions, an open or first position where blade 40 is exposed, an intermediate or third position, and a second or extended position where blade 40 is concealed. These positions are set using actuator 22 in handle 20, shown in FIGS. 9-11. Upon actuation, sheath 50 is moved about 0.45 to about 0.65 inches, preferably from 0.5 to 0.6 inches, and most preferably, 0.54 to 0.57 inches away from blade 50, and towards handle 20, thus exposing the blade.

In the second or extended position, shown in FIG. 9, sheath 50 is fully extended to enclose blade 40. Thus, sheath 50 shields the entirety of blade 40. Sheath 50 is also locked in place to prevent sheath movement. Thus, knife 10 can be moved around and about the surgical site or through the body without the risk of making an undesired or accidental cut which could thereby endanger the patient. In the second or extended position, sheath 50 should extend beyond blade 40 by at least about 0.030 inches, preferably about 0.025 inches, and most preferably about 0.020 inches.

Figure 10:
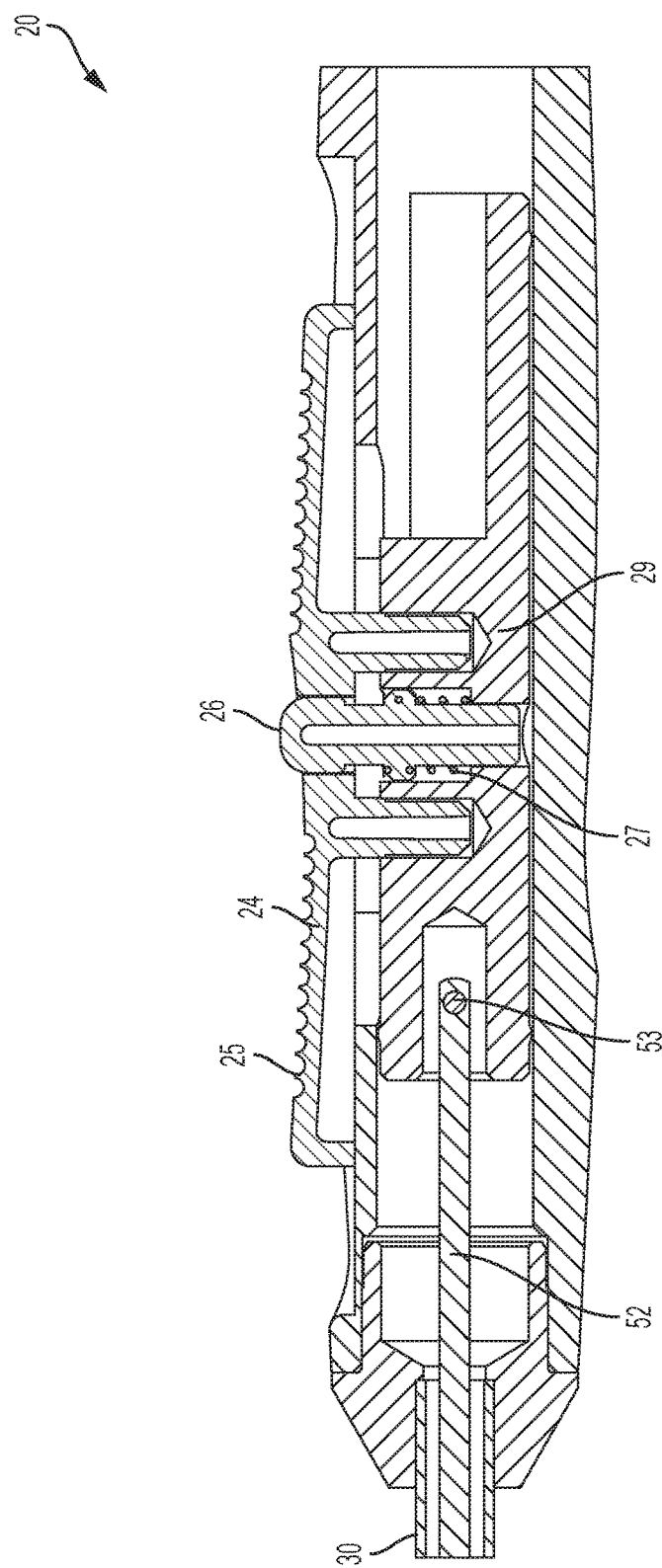
FIG. 10 is a cross section view of the surgical knife of FIG. 2 taken at A-A with the sheath in an intermediate position.

The intermediate (or third) position, shown in FIG. 10, is a plurality of positions that exist between the retracted or first position and extended or second position. In the intermediate position, sheath 50 is not locked in place and is free to move about its predefined path between the first and second positions.

Figure 11:
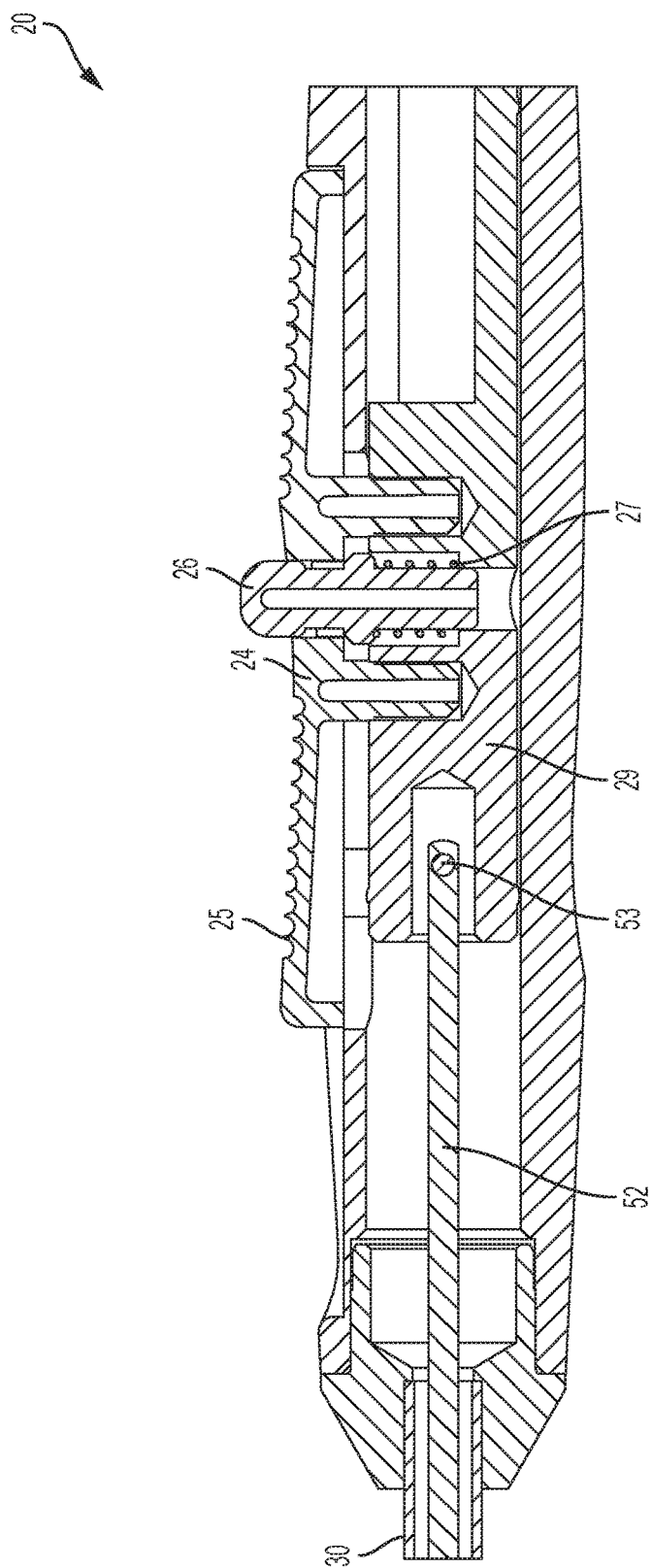
FIG. 11 is a cross section view of the surgical knife of FIG. 2 taken at A-A with the sheath retracted.

In the first position, shown in FIG. 11, sheath 50 is fully retracted to expose blade 40. Sheath 50 is locked in place to prevent sheath movement. Sheath movement is undesirable while a surgeon is operating with the knife. Movement is particularly undesirable as the distance from blade 40 to handle 20 increases, because even slight movement can cause a momentary imbalance and affect the critical positioning and movement of the blade by the surgeon.

FIGS. 12-30 are illustrative of the assembly of knife 10.

Figure 12:
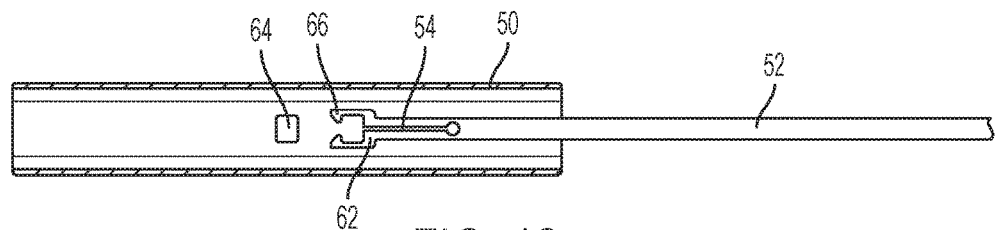
FIG. 12 is the sheath and wire assembly of the present disclosure prior to connecting the sheath with the wire.
Figure 13:
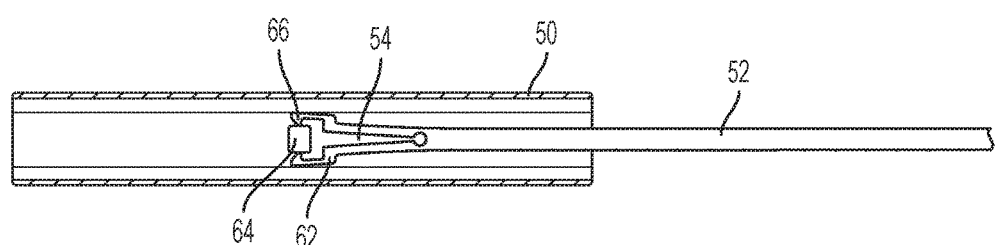
FIG. 13 is the sheath and wire assembly of the present disclosure as the sheath is being connected with the wire.
Figure 14:
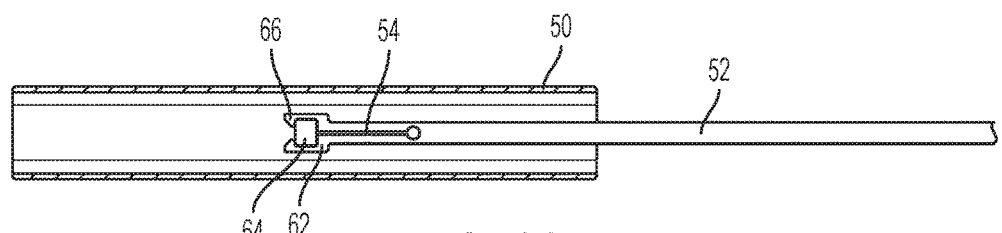
FIG. 14 is the sheath and wire assembly of the present disclosure after to the sheath is connected with the wire.

As shown in FIGS. 12-14, wire 52 is connected or directly attaches to an inner wall of sheath 50, thus forming the sheath and wire assembly. Wire 52 has a bifurcation 54, allowing a C-clip 62 to fit over a bridge 64. Wire 52 is inserted into sheath 50. Sheath 50 is attached to wire 52 by pushing wire 52 against bridge 64 until the wire snaps over the bridge inside the sheath. C-clip 62 can have a feature 66 for assisting or guiding the C-clip 62 around bridge 64 before the C-clip snaps into place.

Figure 15:
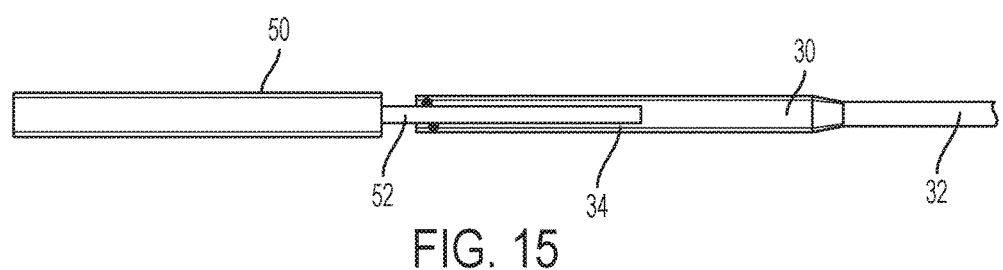
FIG. 15 is the sheath and wire assembly, with the wire positioned through the tube and the sheath positioned over the tube.
Figure 16:
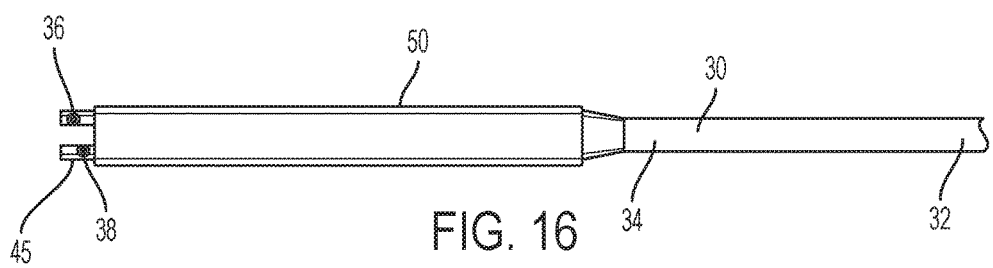
FIG. 16 is the sheath and wire assembly of the present disclosure in a position for attaching the blade.

As shown in FIGS. 15-16, the sheath and wire assembly is mounted to tube 30. Wire 52 is inserted through tube 30 from distal end 34 to proximal end 32. Sheath 50, which is connected to wire 52, is pulled over tube 30 from distal end 34 to proximal end 32. Sheath 50 is moved back further towards proximal end 32 to expose a blade mounting area 45. Blade mounting area 45 includes two bores or holes in tube 30 for mounting blade 40. These two bores or holes are hole 36 and hole 38.

Referring now to FIGS. 17-18, blade 40 is positioned into a flattened part of tube 30. Blade 40 is affixed to tube 30 with a rivet 37 in hole 36 and a rivet 39 in hole 38. Thus, two rivets 37, 39 inserted into two holes 36, 38, respectively, align knife blade 40 with tube 30 and maintain a fixed, rigid relationship therebetween. Once the rivets 37, 39 are staked, tube 30 and blade 40 are connected.

Although shown as and described as a pair of rivets 37, 39, other permanent, and semi-permanent mechanical fastener can be used. Such alternatives can include, but are not limited to, screw, bolt, pin, and the like. In preferred embodiments, a rivet is employed. Advantageously, a rivet is more capable of supporting shear forces than a bolt or screw. Shear forces are defined as the forces perpendicular to longitudinal axis of tube 30. This is because rivets establish a very tight interference fit that is difficult to achieve with other fasteners.

Referring to FIGS. 19-20, proximal end 32 of tube 30 and wire 52 are inserted through front cap 70.

Figure 21:
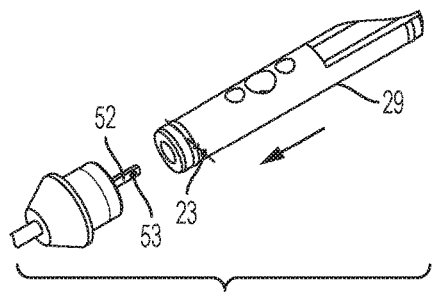
FIG. 21 is an exploded view of an assembly of the wire and inner slide connection.
Figure 22:
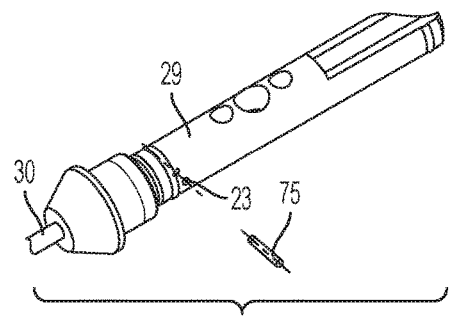
FIG. 22 is an assembled view of the assembly of the wire and inner slide connection of FIG. 21.
Figure 23:
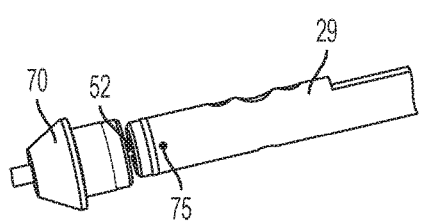
FIG. 23 is a partially assembled view of the assembly of the wire and inner slide connection of FIGS. 21 and 22.

FIGS. 21-23 show the attachment of wire 52 to inner slide 29. Inner slide 29 is positioned over wire 52. A hole 53 in wire 52 is aligned with a hole 23 in inner slide 29. A pin 75 is then inserted in hole 23 and through hole 53, thus connecting wire 52 to inner slide 29.

Figure 24:
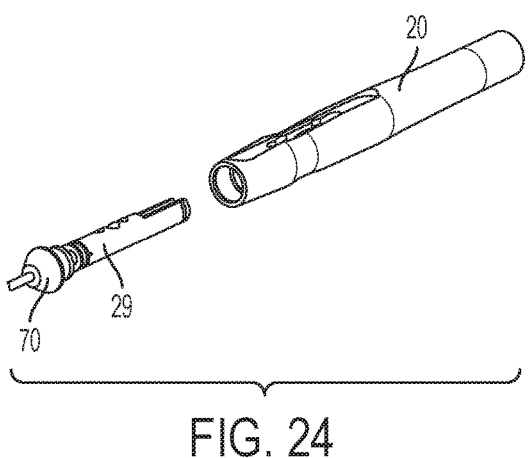
FIG. 24 is an exploded view of an assembly of the inner slide and handle.
Figure 25:
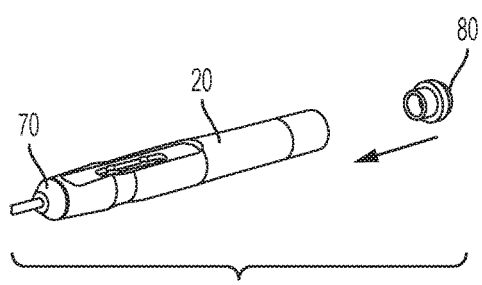
FIG. 25 is an exploded view of an assembly of the rear cap and handle.
Figure 26:
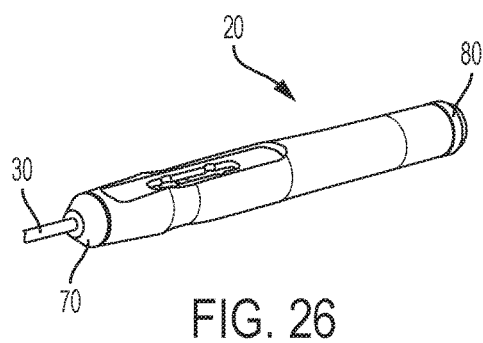
FIG. 26 is an assembled perspective view of the rear cap and handle of FIG. 25.
Figure 27:
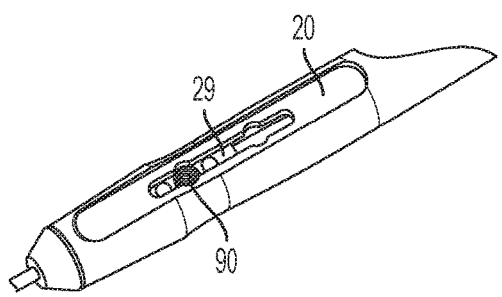
FIG. 27 is a perspective view of the handle assembly with a spring installed.

Referring to FIG. 24, handle 20 is moved over inner slide 29. Handle 20 is then affixed to front cap 70. As illustrated in FIGS. 25-26, a rear cap 80 is then attached to handle 20 at the end opposite front cap 70. As shown in FIG. 27, a spring 90 is inserted through handle 20 and into inner slide 29.

Figure 28:
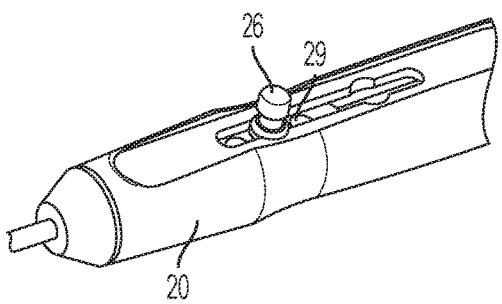
FIG. 28 is a perspective view of the handle assembly with a button installed.
Figure 29:
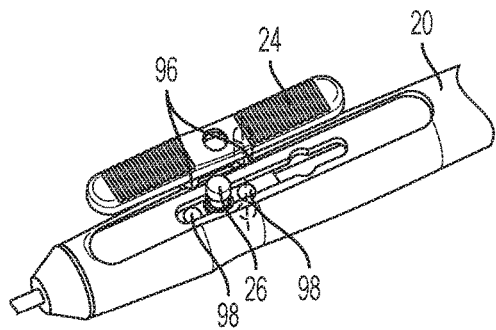
FIG. 29 an exploded view of the handle assembly with a ribbed slide.
Figure 30:
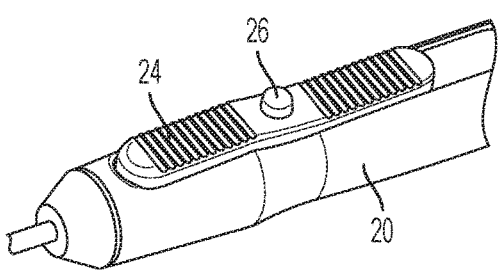
FIG. 30 is a perspective view of the assembled handle assembly of FIG. 29.

In FIG. 28, a button 26 is positioned over spring 90 in handle 20. Finally, as shown in FIGS. 29-30, ribbed slide 24 is inserted onto inner slide 29, over button 26, such that button 26 can be pressed. As illustrated, ribbed slide 24 has two feet 96 that fit into two holes 98 of inner slide 29. However, other variations as to the manner in which ribbed slide 24 attaches to inner slide 29 are envisioned.

Operation of knife is accomplished by depressing the button 26 and moving the ribbed slide 24. By ribbed slide 24 being connected to inner slide 29, inner slide 29 is moved by the movement of ribbed slide 24. Inner slide 29, in turn, causes wire 52 in tube 30 to pull or push sheath 50. When ribbed slide 24 is pushed all the way forward, sheath 50 covers blade 40 entirely, i.e., the closed or extended position as shown in FIGS. 1 and 9. When ribbed slide 24 is pushed all the way back, sheath 50 retracts to expose blade 40. The straight tube embodiment of the present disclosure with tube 30 and the bayonet tube embodiment with tube 130 are both assembled in a similar manner to each other. Both also operate in a similar manner.

It should be noted that where a numerical range is provided herein, unless otherwise explicitly stated, the range is intended to include any and all numerical ranges or points within the provided numerical range and including the endpoints.

It should further be noted that the terms "first", "second", "third", "upper", "lower", and the like can be used herein to modify various elements. These modifiers do not imply a spatial, sequential, or hierarchical order to the modified elements unless specifically stated. Also, when ranges are used herein, the ranges further include all subranges therebetween.

While the present disclosure has been described with reference to one or more exemplary embodiments, it will be understood by those skilled in the art that various changes can be made and equivalents can be substituted for elements thereof without departing from the scope of the present disclosure. In addition, many modifications can be made to adapt a particular situation or material to the teachings of the present disclosure without departing from the scope thereof. Therefore, it is intended that the present disclosure not be limited to the particular embodiment(s) disclosed as the best mode contemplated, but that the present disclosure will include all embodiments falling within the scope of the appended claims.

What is claimed is:

1. A surgical knife comprising:
    an elongated tube having a channel therethrough, the tube having a distal end and a proximal end;
    a blade affixed to the distal end;
    a handle comprising an actuator, wherein the handle is affixed to the proximal end, and wherein the blade, handle, and tube are in a fixed rigid relationship with each other; and
    a sheath connected to a wire, wherein the sheath is retractably slidable over the tube and blade by the wire to expose the blade,
    wherein the sheath is retracted and the blade is exposed in a first position and the sheath is extended and the blade is concealed in a second position, and
    wherein the wire in the tube, the wire has a first end and a second end, and the wire is connected to the sheath at the first end and connected to the actuator at the second end.

2. The surgical knife according to claim 1, wherein the sheath is operatively connected to the actuator.

3. The surgical knife according to claim 1, wherein the tube is straight tube.

4. The surgical knife according to claim 1, wherein the tube is a curved tube.

5. The surgical knife according to claim 1, wherein the sheath is lockable in the first position.

6. The surgical knife according to claim 1, wherein the sheath is lockable in the second position.

7. The surgical knife according to claim 1, wherein the sheath or handle is made of plastic.

8. The surgical knife according to claim 1, wherein the sheath or handle is made of metal.

9. The surgical knife according to claim 1, wherein the blade is connected to the tube with a plurality of rivets.

10. The surgical knife according to claim 1, wherein the blade is treated with at least one coating selected from the group consisting of: titanium carbide, zirconium nitride, titanium nitride, boron carbide, parylene, a silicon based coating, and a polymer based coating.

11. The surgical knife according to claim 1, wherein the surgical knife is adapted for laparoscopic surgery.

12. The surgical knife according to claim 1, wherein an end of the wire is attached to an inside surface of the sheath.

13. The surgical knife according to claim 12, wherein the inside surface of the sheath comprises a protrusion and the wire attaches to the protrusion.

14. The surgical knife according to claim 13, wherein the end of the wire is bifurcated and has a c-clip that attaches around the protrusion.

15. The surgical knife according to claim 1, wherein the wire is flat.

16. The surgical knife according to claim 1, wherein the tube is an s-curved tube.

17. The surgical knife according to claim 1, wherein the sheath extends beyond the blade by at least about 0.020 inches.

18. The surgical knife according to claim 1, wherein the actuator is a slide actuator.

19. A surgical knife comprising:
    an elongated s-curved tube having a channel therethrough, the tube having a distal end and a proximal end;
    a blade affixed to the distal end;
    a handle affixed to the proximal end, wherein the blade, handle, and tube are in a fixed rigid relationship with each other; and
    a sheath retractably slidable over the tube and blade to expose the blade,
    wherein the sheath is retracted and the blade is exposed in a first position and the sheath is extended and the blade is concealed in a second position.

20. A surgical knife comprising:
    an elongated tube having a channel therethrough, the tube having a distal end and a proximal end;
    a blade affixed to the distal end;
    a handle affixed to the proximal end, wherein the blade, handle, and tube are in a fixed rigid relationship with each other; and
    a sheath retractably slidable over the tube and blade to expose the blade,
    wherein the sheath is retracted and the blade is exposed in a first position and the sheath is extended beyond the blade by at least about 0.020 inches to conceal the blade in a second position.

21. A surgical knife comprising:
    an elongated tube having a channel therethrough, the tube having a distal end and a proximal end;
    a blade affixed to the distal end;
    a handle affixed to the proximal end, wherein the blade, handle, and tube are in a fixed rigid relationship with each other;
    a sheath slidable over the tube and blade, the sheath being at least as long as the blade,
    a wire located in the tube, wherein the wire is connected to the sheath and connected to an actuator to commence movement of the wire in the tube; and
    wherein the sheath is retracted and the blade is exposed in a first position and the sheath is extended and the blade is concealed in a second position.

22. The surgical knife according to claim 21, wherein the actuator is located in the handle.

23. The surgical knife according to claim 21, wherein the tube is a straight tube.

24. The surgical knife according to claim 21, wherein the tube is an s-curved tube.

25. The surgical knife according to claim 21, wherein the sheath is lockable in at least one of the first position and the second position.

26. The surgical knife according to claim 21, wherein the actuator is a slide actuator.

27. The surgical knife according to claim 21, wherein the wire is flat.

* * * * *